United States Patent
Bright et al.

(10) Patent No.: US 7,442,737 B2
(45) Date of Patent: Oct. 28, 2008

(54) LOW ACIDITY PHOSPHATE ESTERS

(75) Inventors: Danielle Angrand Bright, New City, NY (US); Edward D. Weil, New York, NY (US); Ronald L. Pirrelli, Mahopac, NY (US)

(73) Assignee: Supresta LLC, Ardsley, NY (US)

( * ) Notice: Subject to any disclaimer, the term of this patent is extended or adjusted under 35 U.S.C. 154(b) by 357 days.

(21) Appl. No.: 10/518,878

(22) PCT Filed: Jun. 24, 2003

(86) PCT No.: PCT/US03/20013

§ 371 (c)(1),
(2), (4) Date: Aug. 1, 2005

(87) PCT Pub. No.: WO04/000922

PCT Pub. Date: Dec. 31, 2003

(65) Prior Publication Data

US 2005/0272837 A1    Dec. 8, 2005

(51) Int. Cl.
*C08K 5/49* (2006.01)

(52) U.S. Cl. ............... 524/115; 524/126; 524/127; 558/156; 558/163

(58) Field of Classification Search ............ 524/115, 524/126, 127; 558/156, 163
See application file for complete search history.

(56) References Cited

U.S. PATENT DOCUMENTS

| | | | |
|---|---|---|---|
| 4,102,859 A | 7/1978 | Eimers et al. | |
| 4,104,433 A | 8/1978 | Kirk et al. | |
| 5,041,596 A | 8/1991 | Bright et al. | |
| 5,616,768 A | 4/1997 | Kawata et al. | |

FOREIGN PATENT DOCUMENTS

| | | |
|---|---|---|
| GB | 1429669 | 3/1976 |
| WO | 02/062808 | 8/2002 |

OTHER PUBLICATIONS

Patent Abstracts of Japan, vol. 004, No. 113 (C-021), Aug. 13, 1980 & JP55-069646, May 26, 1980.
Patent Abstracts of Japan, vol. 1997, No. 12, Dec. 25, 1997 & JP 09-221602, Aug. 26, 1997.

*Primary Examiner*—Rei-tsang Shiao
(74) *Attorney, Agent, or Firm*—Dilworth & Barrese, LLP.

(57) ABSTRACT

A phosphate ester composition of low acidity achieved by treating the phosphate ester of high acidity with an oxetane compound. The phosphate ester can be represented by the formula (I), where Ar is an aryl or alkaryl group, R is an arylene or alkylene group, and n can range from to 0 to about 5.

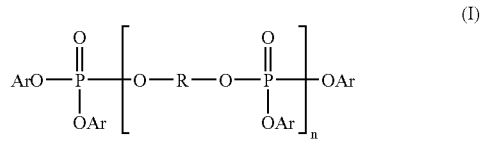

15 Claims, No Drawings

LOW ACIDITY PHOSPHATE ESTERS

Aromatic oligomeric phosphates, which are used as flame-retardants for thermoplastic resins, are made by reaction of $POCl_3$ with a biphenol followed by reaction with phenol (or by the reaction of diphenyl chlorophosphate with a biphenol) in the presence of a Lewis acid catalyst to thereby produce a crude phosphate product. Usually, extensive washing of such a product is needed to remove the catalyst and other acidic impurities that may negatively impact the properties of polymers (i.e, polycarbonates, polyesters, etc.) in which the phosphate ester is placed. Alternatively, the use of epoxides after removal of the catalyst to decrease acidity has been described in U.S. Pat. No. 5,616,768 and in PCT International Patent Application No. PCT/US02/03522, filed Feb. 8, 2002.

It has been found that oxetanes are effective in decreasing the acidity of such phosphate esters. Moreover, it has also been found that an oxetane-treated phosphate ester showed superior hydrolytic stability when compounded with a polycarbonate/ABS resin. While U.S. Pat. No. 4,102,859 teaches the combination of neutral esters of phosphorous acid (i.e., phosphites) and oxetane compounds in plastics, particularly polycarbonate, it does not suggest the combination of phosphate esters and oxetane compounds.

The phosphate ester can be represented by the formula:

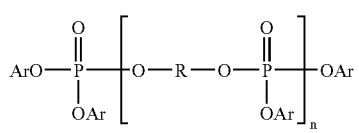

(I)

where Ar is an aryl or alkaryl group, R is an arylene or alkylene group, and n can range from 0 to about 5. Representative R groups include moieties derived from bisphenol A, resorcinol, or neopentyl glycol.

The acid number of the phosphate ester used in the present invention is about 5 mg. KOH/g. or less (for example, about 1 mg. of KOH/g. or less, such as about 0.5 mg. of KOH/g. or less). When the acid number exceeds about 5 mg. of KOH/g., a large amount of oxetane may be needed to obtain the desired low acidity, and this can result in a decrease in flame retardancy of the resin.

The oxetane compound of the present invention is a compound having one or more oxetane groups and is represented by the general structure:

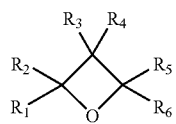

In the above structure, R1-R6 are the same or different and can be selected from hydrogen, alkyl or substituted alkyl, aryl or substituted aryl. Examples of such compounds include: 3-ethyl-3-hydroxymethyl-oxetane (OXT-101 brand, available from Toagosei Co., Ltd.); 3-ethyl-3-((phenoxy)methyl)-oxetane (OXT-211 brand, available from Toagosei Co., Ltd.); and 3-ethyl-3-((2-ethylhexyloxy)methyl)-oxetane (OXT-212 brand, available from Toagosei Co., Ltd.).

Of these, the OXT-101 oxetane product is particularly preferred because of its low molecular weight and the increased reactivity it provides. Depicted below are the formulae for these products:

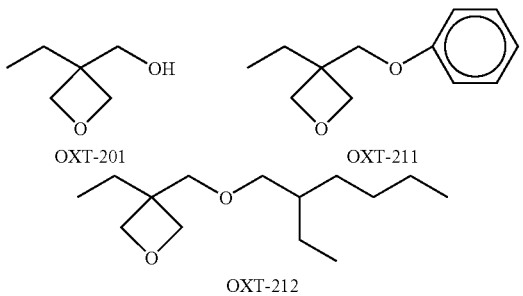

The number of equivalents of oxetane compound in combination with the phosphate ester can be equal to or greater than the number of equivalents of acid present in the crude phosphate ester based on the acid number of that phosphate ester. The crude phosphate ester to be treated in accordance with the present invention can be heated with the selected oxetane compound at temperature ranging from about 40° C. to about 250° C.

The present invention is further illustrated by the following Examples.

EXAMPLE 1

To 203.7 g. of Bisphenol A bis(diphenyl phosphate), having an acid number of 0.555 mg. KOH/g, was added, with stirring at 110° C., 1.0 g. of 3-ethyl-3-hydroxymethyl-oxetane (OXT-101 brand from Toagosei Co., Ltd.). After four hours, the acid number of the resulting phosphate was 0.169 mg. KOH/g.

EXAMPLE 2

To 200 g. of Bisphenol A bis(diphenyl phosphate), having an acid number of 0.555 mg. KOH/g, was added, with stirring at 140° C., 1.0 g. of 3-ethyl-3-hydroxymethyl-oxetane (OXT-101 brand from Toagosei Co., Ltd.). After four hours, the acid number of the resulting phosphate was 0.062 mg. KOH/g.

EXAMPLE 3

To 1005.8 g. of Bisphenol A bis(diphenyl phosphate), having an acid number of 0.531 mg. KOH/g, was added, with stirring at 140° C., 5.0 g. (0.043 mole) of 3-ethyl-3-hydroxymethyl-oxetane (OXT-101 brand from Toagosei Co., Ltd.). After four hours, the acid number of the resulting phosphate was 0.060 mg. KOH/g.

EXAMPLE 4

To 1099.9 g. of Bisphenol A bis(diphenyl phosphate), having an acid number of 0.537 mg. KOH/g, was added, with stirring at 140° C., 8.3 g. (0.043 mole) of 3-ethyl-3-((phenoxy)methyl)-oxetane (OXT-211 brand from Toagosei Co., Ltd.). After four hours, the acid number of the resulting phosphate was 0.14 mg. KOH/g.

EXAMPLE 5

To 1231.9 g. of Bisphenol A bis(diphenyl phosphate), having an acid number 0.537 mg. KOH/g, was added, with stirring at 140° C., 12.1 g. (0.053 mole) of 3-ethyl-3-((2-ethylhexyloxy)methyl)-oxetane (OXT-212 brand from Toagosei Co., Ltd.). After four hours, the acid number of the resulting phosphate was 0.14 mg. KOH/g.

EXAMPLES 5-10

Composites of PC/ABS (in a 4:1 ratio), each containing 12.5% of Bisphenol A bis(diphenyl phosphate), were prepared by melt kneading using a twin screw extruder and pelletizing. The pellets were dried for twelve hours at 70° C.; then were exposed to 100% humidity atmosphere at 107° C. for ninety hours. The change in molecular weight of the polycarbonate was measured after that time. A lower number indicates an increased degree of hydrolytic stability. The results are summarized in Table 1, with Nos. 3-5 relating to the products described in Examples 3-5, above:

TABLE 1

| PC/ABS pellets Containing Sample: | mg. KOH/g. of Sample | % Change in Molecular Weight of PC Resin after 90 hrs. |
|---|---|---|
| 1 (untreated) | 0.5 | 63 |
| 2 (commercial) | 0.05 | 25 |
| 3 (OXT-101) | 0.06 | 12 |
| 4 (OXT-211) | 0.14 | 30 |
| 5 (OXT-212) | 0.14 | 25 |

The foregoing Examples are set forth to merely provide certain preferred embodiments of the present invention and, for that reason, should not be construed in a limiting sense. The scope of protection sought is set forth in the Claims that follow.

What is claimed is:

1. A phosphate ester composition of low acidity, preprared by reading an oxetane compound and a phosphate ester of high acidity, wherein said phosphate ester has the following formula:

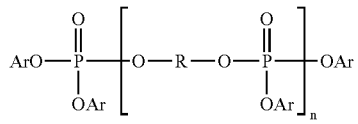

where Ar is an aryl or alkaryl group, R is an arylene group, and n can range from 0 to about 5 and said oxentane compound has the following formula:

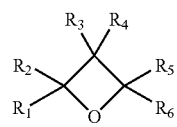

where $R_1$ to $R_6$ are each the same or different and are selected from the group consisting of hydrogen, alkyl, substituted alkyl, aryl, and substituted aryl.

2. A composition according to claim 1 where Ar is phenyl and —O—R—O— is a bisphenol A moiety.

3. A composition according to claim 1 where Ar is phenyl and —O—R—O— is a resorcinol moiety.

4. A composition according to claim 1 in which the oxetane compound is 3-ethyl-3-hydroxymethyl-oxetane.

5. A composition according to claim 1 in which the number of equivalents of oxetane compound is equal to or greater than the number of equivalents of acid present in the crude phosphate ester based on the acid number of the crude phosphate ester.

6. A flame-retardant thermoplastic composition containing the phosphate ester composition of claim 1.

7. A process for making a phosphate ester composition of low acidity according to claim 1, which comprises treating a phosphate ester of acid number greater than 0.1 mg. KOH/g. with an oxetane compound at elevated temperature.

8. A process according to claim 7 in which the phosphate ester is heated with the oxetane at temperature ranging from about 40° C. to about 250° C.

9. A process according to claim 7, in which the phosphate ester is represented by the formula:

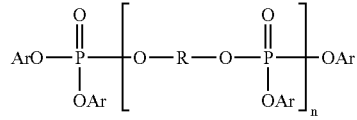

where Ar is an aryl or alkaryl group, R is an arylene or alkylene group, and n ranges from 0 to about 5.

10. A process according to claim 9 where Ar is phenyl and —O—R—O— is a bisphenol A moiety.

11. A process according to claim 9 where Ar is phenyl and —O—R—O— is a resorcinol moiety.

12. A process according to claim 9 where Ar is phenyl and —O—R—O— is a neopentyl glycol moiety.

13. A process according to claim 7 in which the oxetane compound is 3-ethyl-3-hydroxymethyl-oxetane.

14. A process according to claim 7 in which the number of equivalents of oxetane compound is equal to or greater than the number of equivalents of acid present in the crude phosphate ester based on the acid number of the crude phosphate ester.

15. The phosphate ester according to claim 1 wherein the oxetane compound is 3-ethyl-3((phenoxy)methyl)-oxetane or 3-ethyl-3-((2-ethylhexyloxy)methyl)-oxetane.

* * * * *